US010564144B2

(12) United States Patent
Garaj et al.

(10) Patent No.: US 10,564,144 B2
(45) Date of Patent: Feb. 18, 2020

(54) NANOMETRIC MATERIAL HAVING A NANOPORE ENABLING HIGH-SENSITIVITY MOLECULAR DETECTION AND ANALYSIS

(75) Inventors: Slaven Garaj, Cambridge, MA (US); Jene A. Golovchenko, Lexington, MA (US); Daniel Branton, Lexington, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 1133 days.

(21) Appl. No.: 13/419,383

(22) Filed: Mar. 13, 2012

(65) Prior Publication Data

US 2012/0234679 A1    Sep. 20, 2012

Related U.S. Application Data

(63) Continuation-in-part of application No. PCT/US2010/049238, filed on Sep. 17, 2010.
(Continued)

(51) Int. Cl.
*G01N 33/487* (2006.01)

(52) U.S. Cl.
CPC .............. *G01N 33/48721* (2013.01)

(58) Field of Classification Search
CPC ............. B82Y 30/00; G01N 33/48721; G01N 15/1056; G01N 2015/0038; C12Q 2565/631
See application file for complete search history.

(56) References Cited

U.S. PATENT DOCUMENTS

2004/0033492 A1    2/2004  Chen
2005/0136408 A1*   6/2005  Tom-Moy ............ C12Q 1/6816
                                                      435/6.12
(Continued)

FOREIGN PATENT DOCUMENTS

| CN | 101694474 A | * | 4/2010 | ............. B82Y 15/00 |
| CN | 102095768 A | * | 6/2011 | ............. B82Y 15/00 |
| WO | 2009035647 A1 |  | 3/2009 | |

OTHER PUBLICATIONS

S. Liu et al., Fast and controllable fabrication of suspended graphene nanopore devices, Nanotechnology, vol. 23, pp. 085301-1-085301-6 (Feb. 1, 2012). (Year: 2012)*
(Continued)

*Primary Examiner* — Maris R Kessel
(74) *Attorney, Agent, or Firm* — Theresa Lober

(57) ABSTRACT

There is provided a substantially bare, self-supported single-layer graphene membrane including a nanopore extending through a thickness of the graphene membrane from a first to a second membrane surface opposite the first graphene membrane surface. A connection from the first graphene membrane surface to a first reservoir provides, at the first graphene membrane surface, a species in an ionic solution to the nanopore, and a connection from the second graphene membrane surface to a second reservoir is provided to collect the species and ionic solution after translocation of the species and ionic solution through the nanopore from the first graphene membrane surface to the second graphene membrane surface. An electrical circuit is connected on opposite sides of the nanopore to measure flow of ionic current through the nanopore in the graphene membrane.

24 Claims, 7 Drawing Sheets

Related U.S. Application Data

(60) Provisional application No. 61/243,607, filed on Sep. 18, 2009, provisional application No. 61/355,528, filed on Jun. 16, 2010.

(56) References Cited

U.S. PATENT DOCUMENTS

| | | | | |
|---|---|---|---|---|
| 2006/0003458 | A1* | 1/2006 | Golovchenko | C12Q 1/6811 436/86 |
| 2006/0063171 | A1* | 3/2006 | Akeson | B01L 3/502707 435/6.11 |
| 2008/0041733 | A1* | 2/2008 | Hibbs | G01N 33/48721 205/775 |
| 2010/0327847 | A1* | 12/2010 | Leiber | B82Y 15/00 324/71.1 |
| 2012/0037919 | A1* | 2/2012 | Xu | B82Y 15/00 257/76 |
| 2013/0037410 | A1* | 2/2013 | Xu | B82Y 15/00 204/601 |

OTHER PUBLICATIONS

C. A. Merchant, et al., DNA Translocation through Graphene Nanopores, Nano Lett., vol. 10, pp. 2915-2921 (2010) (Year: 2010).*

PCT/US2010/049238, International Search Report, PCT/ISA/210 first sheet, second sheet pp. 1-2, and patent family annex, Apr. 21, 2011.

PCT/US2010/049238, Written Opinion of the International Searching Authority, PCT/ISA/237 cover sheet, Box No. 1 sheet, Box No. III sheet, Box No. V sheet, Separate Sheet-Sheets 1-4, Mar. 18, 2012.

Reina et al., "Large area, few-layer graphene films on arbitrary substrates by chemical vapor deposition," Nano Letters, ACS, vol. 9, No. 1, pp. 30-35, Jan. 1, 2008.

Sint et al., "Selective Ion Passage through Functionalized Graphene Nanopores," Jnl. of the American Chem. Soc., vol. 131, No. 27, pp. 16448-16449, Nov. 14, 2008.

Zwolak et al., "Colloquium: Physical Approaches to DNA Sequencing and Detection," Reviews of Modern Physics Published for the American Physical Society by the American Inst. of Physics USA, vol. 80, No. 1, pp. 141-165, Jan. 2, 2008.

Branton et al., "The potential and challenges of nanopore sequencing," Nature Biotechnology, vol. 26, No. 10, pp. 1146-1153, Oct. 1, 2008.

Michael D. Fischbein and Marija Drndic, Electron Beam Nanosculpting of Suspended Graphene Sheets, 3 pages, Sep. 16, 2008, Applied Physics Letters.†

\* cited by examiner
† cited by third party

NANOMETRIC MATERIAL HAVING A NANOPORE ENABLING HIGH-SENSITIVITY MOLECULAR DETECTION AND ANALYSIS

CROSS-REFERENCE TO RELATED APPLICATIONS

This is a continuation-in-part of co-pending International Application PCT/US/2010/049238, with an international filing date of Sep. 17, 2010. This application claims the benefit of U.S. Provisional Application No. 61/243,607, filed Sep. 18, 2009, the entirety of which is hereby incorporated by reference. This application also claims the benefit of U.S. Provisional Application No. 61/355,528, filed Jun. 16, 2010, the entirety of which is hereby incorporated by reference.

STATEMENT REGARDING FEDERALLY SPONSORED RESEARCH

This invention was made with Government support under Contract No. 2R01HG003703-04 awarded by the NIH. The Government has certain rights in the invention.

BACKGROUND

This invention relates generally to molecular detection and analysis, and more particularly relates to configurations for a nanopore arranged to detect molecules translocating through the nanopore.

The detection, characterization, identification, and sequencing of molecules, including biomolecules, e.g., polynucleotides such as the biopolymer nucleic acid molecules DNA, RNA, and peptide nucleic acid (PNA), as well as proteins, and other biological molecules, is an important and expanding field of research. There is currently a great need for processes that can determine the hybridization state, configuration, monomer stacking, and sequence of polymer molecules in a rapid, reliable, and inexpensive manner. Advances in polymer synthesis and fabrication and advances in biological development and medicine, particularly in the area of gene therapy, development of new pharmaceuticals, and matching of appropriate therapy to patient, are in large part dependent on such processes.

In one process for molecular analysis, it has been shown that molecules such as nucleic acids and proteins can be transported through a natural or solid-state nano-scale pore, or nanopore, and that characteristics of the molecule, including its identification, its state of hybridization, its interaction with other molecules, and its sequence, i.e., the linear order of the monomers of which a polymer is composed, can be discerned by and during transport through the nanopore. Transport of a molecule through a nanopore can be accomplished by, e.g., electrophoresis, or other translocation mechanism.

In one particularly popular configuration for molecular analysis with a nanopore, the flow of ionic current through a nanopore is monitored as a liquid ionic solution, and molecules to be studied that are provided in the solution, traverse the nanopore. As molecules in the ionic solution translocate through the nanopore, the molecules at least partially block flow of the liquid solution, and the ions in the solution, through the nanopore. This blockage of ionic solution can be detected as a reduction in measured ionic current through the nanopore. With a configuration that imposes single-molecule traversal of the nanopore, this ionic blockage measurement technique has been demonstrated to successfully detect individual molecular nanopore translocation events.

Ideally, this ionic blockage measurement technique for molecular analysis, like others that have been proposed, should enable molecular characterization with high sensitivity and resolution on the scale of single monomer resolution. Unambiguous resolution of individual monomer characteristics is critical for reliable applications such as biomolecular sequencing applications. But this capability has been difficult to achieve in practice, particularly for solid-state nanopore configurations. It has been found that the length of a solid state nanopore, determined by the thickness of a material layer or layers in which the nanopore is formed, impacts the nature of molecular traversal of the nanopore, and directly limits the sensitivity and the resolution with which molecules in the nanopore can be detected and analyzed.

SUMMARY OF THE INVENTION

There is provided a nanopore sensor that overcomes the sensitivity and resolution limitations of conventional nanopore sensors. In one example of such there is provided a nanopore sensor including a self-supported nanometric material having a thickness, between a first material surface and a second material surface opposite the first material surface, that is less than about 5 nm. A nanopore extends through the material thickness between the first and second material surfaces. The nanopore has a diameter that is greater than the material thickness. There is a connection from the first material surface to a first reservoir to provide, at the first material surface, a species in an ionic solution to the nanopore, and there is a connection from the second material surface to a second reservoir to collect the species and ionic solution after translocation of the species and ionic solution through the nanopore from the first material surface to the second material surface. An electrical circuit is connected to monitor translocation of the species in the ionic solution through the nanopore in the solid state material. having a thickness between a first material surface and a second material surface opposite the first material surface that is less than about 1 nm.

This nanopore sensor can be provided as, e.g., a graphene nanopore sensor. Here there is provided a substantially bare, self-supported single-layer graphene membrane including a nanopore extending through a thickness of the graphene membrane from a first graphene membrane surface to a second graphene membrane surface opposite the first graphene membrane surface. A connection from the first graphene membrane surface to a first reservoir provides, at the first graphene membrane surface, a species in an ionic solution to the nanopore, and a connection from the second graphene membrane surface to a second reservoir is provided to collect the species and ionic solution after translocation of the species and ionic solution through the nanopore from the first graphene membrane surface to the second graphene membrane surface. An electrical circuit is connected on opposite sides of the nanopore to measure flow of ionic current through the nanopore in the graphene membrane.

In a further graphene nanopore sensor a self-supported, substantially bare, single-layer graphene membrane includes a nanopore extending through a thickness of the graphene membrane from a first graphene membrane surface to a second graphene membrane surface opposite the first graphene surface and having a diameter that is less than about 3 nm and greater than the graphene thickness. An electrical circuit is connected on opposite sides of the nanopore to measure flow of ionic current through the nanopore in the graphene membrane.

These configurations enable a method for evaluating a polymer molecule in which the polymer molecule to be evaluated is provided in an ionic solution. The polymer molecule in the ionic solution is translocated through a nanopore in a substantially bare, self-supported single-layer graphene membrane from a first graphene membrane surface to a second graphene membrane surface opposite the first graphene surface and the flow of ionic current through the nanopore in the graphene membrane is monitored.

These sensor arrangements and sensing methods enable high-resolution, high-sensitivity molecular detection and analysis, thereby achieving sensing of closely-spaced monomers in a polymer and accordingly, sequentially resolving the different ionic blockages caused by each monomer in, for example, a strand of a DNA polymer. Other features and advantages of the invention will be apparent from the following description and accompanying figures, and from the claims.

DETAILED DESCRIPTION

Figure 1:
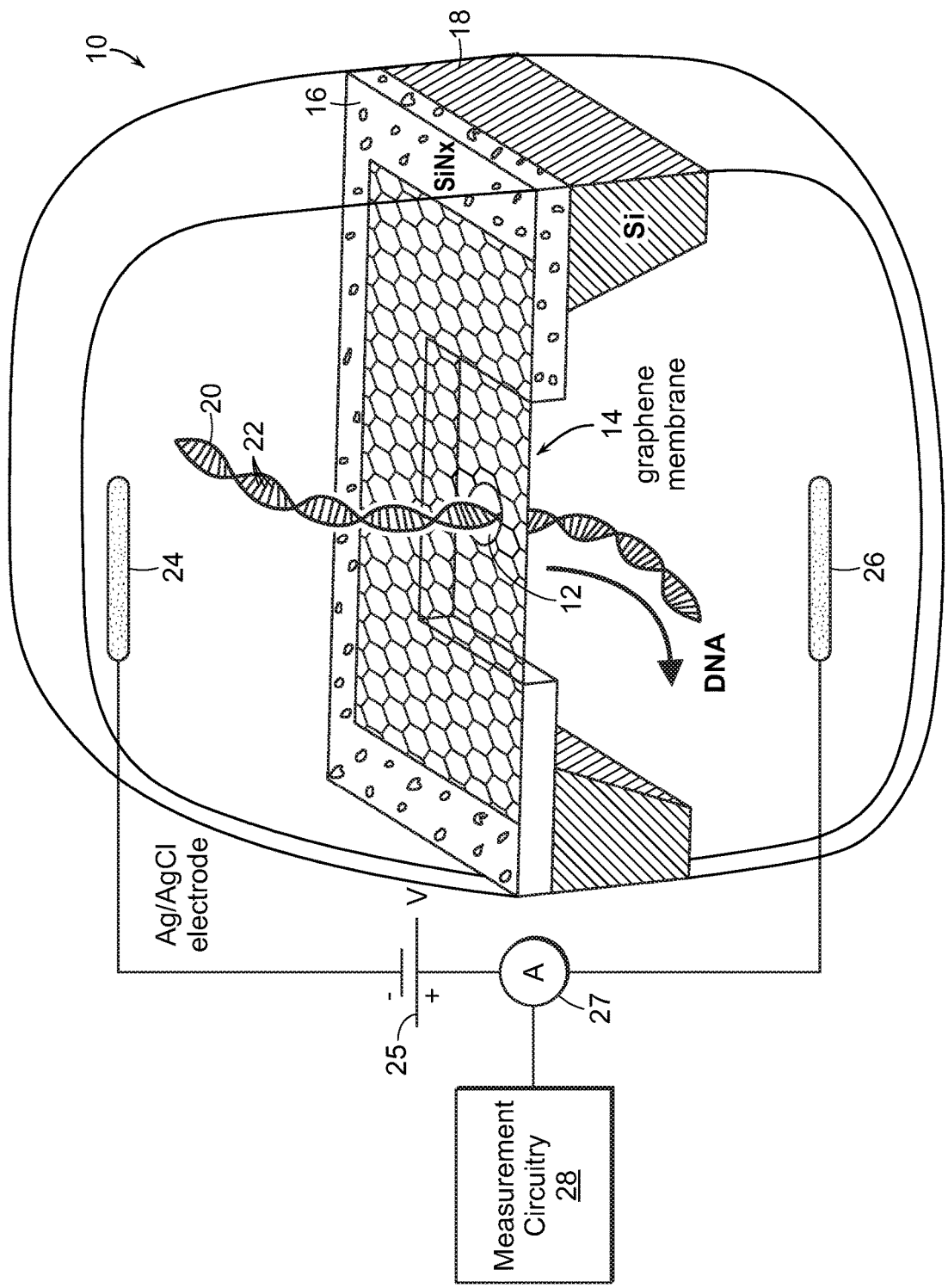
FIG. 1 is a schematic perspective view of an example graphene nanopore device for detecting molecules by measurement of ionic flow through the nanopore.

FIG. 1 is a schematic perspective view of an example graphene nanopore molecular characterization device 10. For clarity of discussion, device features illustrated in FIG. 1 are not shown to scale. As shown in FIG. 1, in the device there is provided a nano-scale aperture, or nanopore 12, in a bare, single-layer graphene membrane 14. The graphene membrane is self-supported, meaning that there are no structures under the extent of the membrane to support the membrane. At the edges of the membrane there can be provided, e.g., a support frame 16, which in turn can be provided on a support substrate or other structure 18. The self-supported bare graphene membrane is configured in a fluidic cell such that on the first, or cis, side of the graphene membrane is a connection to a first liquid reservoir or liquid supply containing a liquid solution including molecules 20 to be characterized, and on the second, or trans, side of the graphene membrane is a connection to a second liquid reservoir, into which characterized molecules are transported by translocation through the graphene nanopore 12.

In one application of the graphene nanopore, shown in the figure, the molecules 20 to be characterized comprise single-stranded DNA molecules (ssDNA) having a sequence of nucleoside bases 22 to be characterized, for example, by determining the identity of the sequence of bases along each ssDNA backbone. For clarity of discussion this sequencing example will be employed in the following description, but such is not the exclusive application of the graphene nanopore characterization device. In addition, the sequencing operation described below is not limited to the example of DNA; the polynucleotide RNA can similarly be characterized. The molecular characterization enabled by the graphene nanopore device includes a wide range of analyses, including, e.g., sequencing, hybridization detection, molecular interaction detection and analysis, configuration detection, and other molecular characterizations. The molecules 20 to be characterized can include, in general, any molecule, including polymers and biomolecules such as proteins, nucleic acids such as the polynucleotides DNA and RNA, sugar polymers, and other biomolecules. The discussion below is therefore not intended to be limiting to a particular implementation, but provides details of one example in a range of embodiments for molecular characterization.

There is provided for the graphene nanopore of FIG. 1 an arrangement of features for causing molecules 20 to traverse the nanopore through the bare, self-supported, single-layer graphene membrane. For example, there can be provided silver chloride electrodes 24, 26 immersed in the solutions on either side of the graphene membrane 14, for controlling the voltage of each solution across the graphene membrane. Application of a voltage bias 25 between the electrodes in the two solutions on opposing sides of the membrane causes molecules, e.g., ssDNA molecules, provided in the solution on the first, or cis, side of the membrane, to be electrophoretically driven into and through the nanopore 12 to the solution on the second, or trans side of the membrane, because the DNA backbone is negatively charged when in solution.

The inventors herein have made a surprising discovery that the ionic resistivity perpendicular to the plane of a bare, single-layer graphene membrane separating two ionic solution-filled reservoirs is extremely large, making it possible to establish a significant voltage bias across the graphene membrane, between the two solutions, in the manner described above. As explained further in the experimental discussion below, this discovery enables the configuration of FIG. 1 in which electrical control of the potential across a single layer of graphene can be maintained in a manner required for molecular electrophoresis.

It is further discovered that a bare, single-layer graphene membrane is sufficiently mechanically robust to operate as a structural barrier between two solution-filled reservoirs whether or not these reservoirs are in communication directly with each other through a nanopore in the graphene membrane that is supported only at its edges by a frame, i.e., that is self-supported across its extent. As a result, a nanopore-articulated membrane of a single bare graphene layer can operate to separate two ionic solution-filled reservoirs, using methods known to those familiar with the nanopore field, for application of a voltage bias between the two ionic solutions on the cis and trans sides of the bare graphene membrane to electrophoretically drive molecules through the nanopore.

Other techniques and arrangements can be employed for drawing molecules through the nanopore, and no particular technique is required. Further details and examples for electrophoretic driving of molecular translocation through a nanopore are provided in "Molecular and Atomic Scale Evaluation of Biopolymers, U.S. Pat. No. 6,627,067, to Branton et al., issued Sep. 30, 2003, the entirety of which is hereby incorporated by reference.

As shown in FIG. 1, there can be provided circuitry 27, 28 for measuring changes in ionic current flow between the cis and trans sides of the graphene membrane, through the nanopore 12. With this configuration, translocation of molecules through the nanopore 12 can be detected and based on the detection, can be analyzed as the molecules are driven through the nanopore. This molecular detection technique is but one of a wide range of detection techniques that can be employed with the graphene membrane and nanopore. Tunneling current between electrodes, e.g., between carbon nanotubes or other probes articulated at the nanopore, conductance changes in probes or in the graphene membrane itself, or other molecular detection technique can be employed, as described, e.g., in "Molecular Characterization with Carbon Nanotube control, U.S. Pat. No. 7,468,271 by Golovchenko et al., issued Dec. 23, 2008, the entirety of which is hereby incorporated by reference.

Considering specifically the technique of molecular detection by ionic current flow measurement, the inventors herein have made a surprising discovery that the ionic current through the nanopore of the bare, single-layer graphene membrane, when empty of a translocating species, and the ionic current flow through the nanopore, when blocked by a molecule that is in the nanopore, are both approximately 3 times greater than the ionic current flow through a similar-diameter nanopore in any other known lipid or solid state membrane interface. This significantly greater ionic current flow through a nanopore in the bare, single-layer graphene membrane, compared to a similar-diameter biopore or nanopore in another solid state membrane, is understood by the inventors to be due to the thinness of the graphene membrane and correspondingly, the length of the nanopore through the membrane.

A bare graphene membrane is a single-atom layer of a hexagonal carbon lattice that is therefore atomically thin, being only about 0.3 nm thick. At this thickness, ionic flow through a nanopore in the bare, single-layer graphene membrane can be characterized in a regime in which the length of the nanopore is much less than the diameter of the pore. In this regime, the ionic conductance of the nanopore is proportional to the nanopore diameter, d, and the ionic current density through the nanopore is sharply peaked at the periphery of the nanopore, that is, at the edge of the nanopore, compared with the current density at the middle of the nanopore. In contrast, nanopores having a length that is greater than the nanopore diameter are characterized by an ionic conductance that is proportional to the nanopore area, and that is homogeneous across the nanopore diameter, with ionic conductivity uniformly flowing down through the middle of the nanopore as well as at the periphery of the nanopore.

Figure 2A:
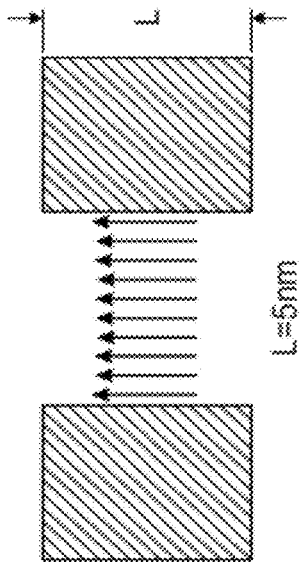
FIGS. 2A-2E are schematic side views of six theoretical nanopores in membranes, each nanopore of 2.4 nm in diameter and ranging in nanopore length from 0.6, nm, 1 nm, 2 nm, 5 nm and 10 nm, respectively, with the average ionic current density at various regions through each nanopore represented the lengths of arrows shown in the nanopores.
Figure 2B:
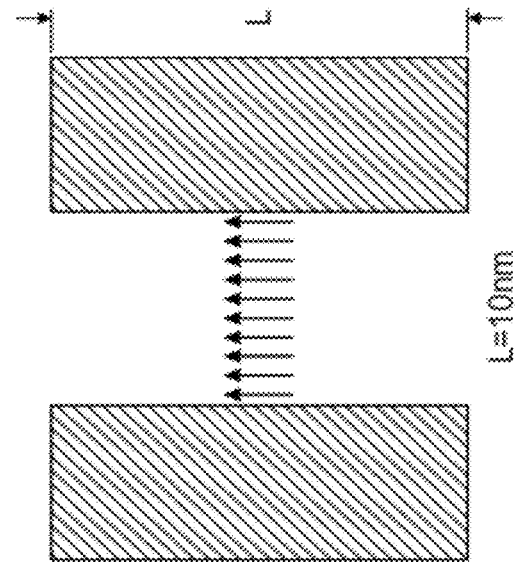
Figure 2C:
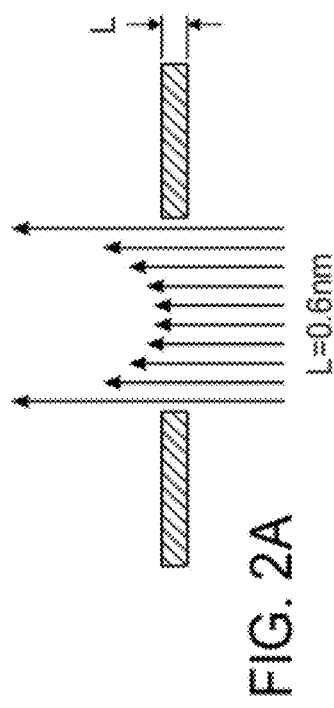
Figure 2D:
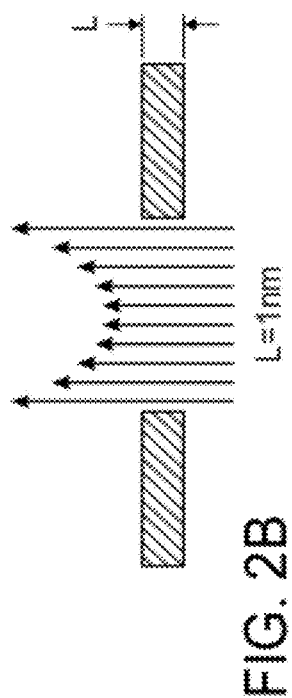
Figure 2E:
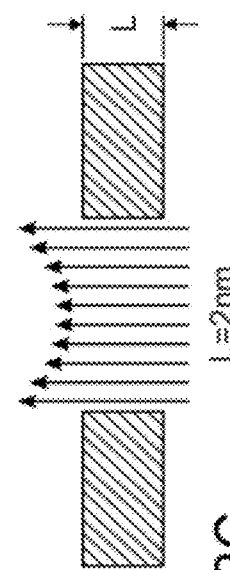

The clear distinction between nanopore conductances in these two nanopore length regimes are illustrated in FIGS. 2A-2E. Referring to those figures, there are shown representations of the average current density at ten points across nanopores each having a diameter of 2.4 nm and having a length of 0.6 nm, 1 nm, 2 nm, 5 nm, and 10 nm, respectively. The relative lengths of the arrows in the figures indicate the relative average current density in the region in a nanopore that is represented by the location of each arrow. As shown in FIGS. 2A-2C, for nanopore lengths that are less than the nanopore diameter of 2.4 nm, the current density is peaked at the nanopore periphery. As the nanopore length approaches the nanopore diameter, the conductance across the nanopore becomes more uniform. When the nanopore length is greater than the nanopore diameter, as in FIGS. 2D and 2E, the ionic conductance is uniformly homogenous across the nanopore, with no preference for the nanopore periphery. The local current density within different regions of the nanopores becomes more and more homogeneous as the nanopore length is increased.

As a consequence, a nanopore in a bare, self-supported single-layer graphene membrane in which the nanopore diameter is greater than the nanopore length exhibits a total ionic conductance, in an unobstructed state, that is significantly greater than the total conductance of a nanopore of equal diameter in a membrane having a thickness greater than the nanopore diameter. Other conditions being equal, the greater conductance results in a significantly greater total ionic current through an open nanopore of a given diameter in a membrane thinner than the diameter than in an open nanopore of equal diameter in a membrane thicker than the diameter. The larger ionic currents through the graphene membrane facilitate high-accuracy measurement of ionic current flow through the nanopore.

Because the ionic current through nanopores having a length less than nanopore diameter is primarily at the nanopore periphery rather than through the nanopore center axis, small changes in the diameter of molecules centrally traversing the nanopore have an enormous effect on the change in ionic current flow. This is due to the fact that differences in the diameters of molecules are manifested at the nanopore edge, where ionic current flow is greatest for short-length nanopores, rather than in the nanopore center, where for short-length nanopores ionic current is lower. As a result, a bare, single-layer graphene nanopore having a length less than the nanopore diameter is more sensitive to molecularly-dimensioned particles or differences in differently-dimensioned particles, molecules, or their components than are nanopores having a length greater than the nanopore diameter.

Figure 3:
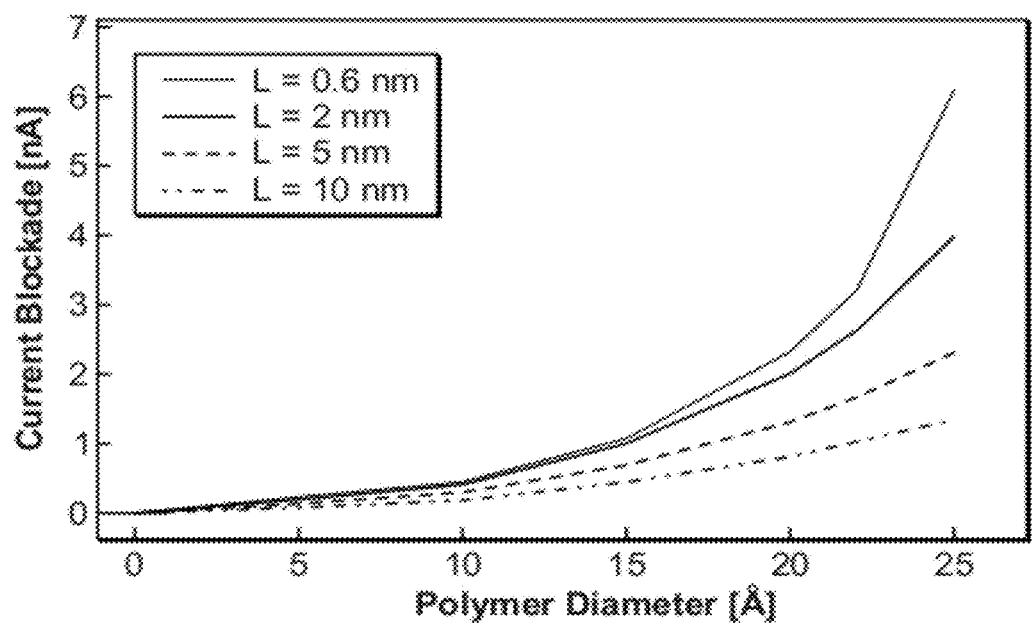
FIG. 3 is a plot of ionic current blockade, defined as the absolute value of the difference between the ionic current through an unblocked nanopore and the ionic current through the same nanopore when blocked with a molecule of the indicated diameter, for a 3M KCl ionic solution and a nanopore bias of 160 mV, for nanopores having a 2.5 nm diameter and effective lengths of 0.6 nm, 2 nm, 5 nm, and 10 nm.

The consequence of this consideration is shown quantitatively in FIG. 3, in which there is plotted the computed ionic current blockage level in a nanopore as a function of the diameter of polymer molecules centrally traversing nanopores having a diameter of 2.5 nm and having effective lengths of 0.6 nm, 2 nm, 5 nm, and 10 nm. The computed current blockage is the absolute value of the difference between the ionic current though an unblocked nanopore, i.e., no polymer molecule in the nanopore, and the ionic current through the same nanopore when blocked with a polymer of the indicated diameter. The plots assume molecular translocation with an ionic solution of 3M KCl and a voltage bias of 160 mV between cis and trans sides of the nanopore. As shown in the plots here, the ionic current through the nanopores demonstrates increasing sensitivity to changes in diameter of translocating molecules as the length of the nanopores is decreased.

The inventors have further discovered that the sensitivity in a nanopore's conductivity to changes in translocating molecules' diameters is maximized when the nanopore diameter is set to be as close as possible to the diameter of the translocating molecules. This condition is true for nanopores of any length. For example, as shown in the plots of FIG. 3, for nanopores of 2.5 nm in diameter, as the translocating molecule diameter approaches the nanopore diameter, the current blockage rises, even where the nanopore length is greater than the nanopore diameter. But for nanopores in which nanopore length is less than nanopore diameter, namely 2 nm and 0.6 nm in the plotted data, it is shown that such short-length nanopores are much more acutely sensitive to small changes in translocating molecule diameter as the molecule diameter approaches the nanopore diameter. For these nanopores the blockade currents rise exponentially with increases in blocking molecule diameter. For the 5 nm and 10 nm-long nanopores, which are larger than the nanopore diameter, the blockade currents rise only in a near linear manner, even as blocking molecules' diameters approach the nanopore diameter.

Thus, the resolution of closely-spaced differences in translocating molecules' diameters is preferably maximized by providing in a single-layer graphene membrane a nanopore having a diameter that is both greater than the membrane edge thickness but not much greater than the diameter expected for molecules that are translocating the nanopore, e.g., no more than 5% greater. To determine this second condition for nanopore diameter for a given application, there can be carried out an analysis like that described in the Example below. Briefly, in such an analysis, there is determined via, e.g., a Laplace equation, the ionic current density of the ionic solution that will be used for molecular translocation, the desired sensitivity of molecular translocation detection is set, and the general requirements for what nanopore diameter is feasible are determined. Based on these factors, and the overriding constraint that the nanopore diameter is greater than the membrane thickness, a nanopore diameter that optimizes all of these factors can then be selected.

In conducting such a nanopore design analysis, the widest feature of a molecular structure that exists along the length of a molecule can be considered as setting the molecular diameter. The nanopore diameter that optimizes the factors above can then be specified, particularly to be no more than about 5% greater than the widest molecular feature. Given that a nanopore may not be optimally circular, the smallest extent across the expanse of a nanopore can be considered the diameter of the nanopore for this design purpose. This smallest nanopore extent is to be no more than about 5% greater than the widest molecular feature of a molecular structure to translocate the nanopore.

The inventors have further discovered that the electrical noise from a bare, self-suspended single-layer graphene nanopore separating two electrically-biased ionic solution-filled reservoirs is proportionally no greater than the electrical noise from any other solid state nanopore. As a result, given that the ionic current change, i.e., ionic blockage, through a graphene nanopore is greater during traversal of a molecule of any given diameter than it is in other known nanopores having a length greater than the nanopore diameter, a bare, single-layer graphene nanopore can produce a better signal-to-noise ratio than other known nanopores because the greater the number of ions counted per unit time, or per traversing nucleobase, will be more precise than at a lesser count rate. These discoveries, together with graphene's known chemical inertness and exceptionally great strength, establish a nanopore-articulated bare, single-layer graphene membrane as a superior interface for molecular detection and characterization.

As a result of these discoveries, it is preferred that the membrane be provided as a single layer of graphene that is bare, i.e., that is not coated on either side with any material layer or species that adds to the graphene membrane thickness. In this state, the thickness of the membrane is minimized and is safely in the short-length nanopore regime in which peripheral ionic current flow is maximized and in which the nanopore conductivity as a function of changes in the analytes physical dimensions is maximized. The very short nanopore length provided by the graphene membrane also makes it possible for a graphene nanopore to sense closely-spaced monomers in a polymer and thus to sequentially resolve the different ionic blockages caused by each monomer in, for example, a strand of a DNA polymer.

It is recognized that a single-layer graphene membrane has an affinity for many molecules such as polymer molecules like DNA and RNA. It can therefore be expected that DNA, RNA, and other like molecules have a tendency to adsorb onto a bare graphene membrane preferentially. It is preferred that the absorptive properties of the graphene surface be at least partially inhibited with an appropriate environment and/or surface treatment that maintains the membrane in a bare state without added surface layers.

For example, there can be provided an ionic solution that is characterized by a pH greater than about 8, e.g., between about 8.5 and 11 and that includes a relatively high salt concentration, e.g., greater than about 2M and in the range from 2.1M to 5M. By employing a basic solution of high ionic strength, adherence of molecules to the surface of the bare graphene membrane is minimized. Any suitable selected salt can be employed, e.g., KCl, NaCl, LiCl, RbCl, $MgCl_2$, or any readily soluble salt whose interaction with the analyte molecule is not destructive.

In addition, as explained in detail below, during synthesis and manipulation of the graphene membrane it is preferred that extreme care be taken to maintain the membrane in a pristine condition such that substantially no residues or other species, which might attract molecules to the graphene surface, are present. It is also recognized that in operation, the graphene membrane can be electrically manipulated to repel molecules from the graphene surface. For example, given translocation of negatively-charged DNA molecules through a nanopore in a graphene membrane, a graphene membrane can itself be electrically biased at a negative potential that repels the negatively-charged DNA molecule. Here electrical contact can be made to the graphene membrane in any suitable manner that enables application of a selected voltage. In such a scenario, the voltage between ionic solutions on either side of the graphene membrane can be set sufficiently high to produce an electrophoretic force which overcomes the repulsion at the graphene surface to cause DNA translocation through the nanopore rather than adsorption at the graphene surface.

Turning to methods for producing the graphene nanopore device, a single layer of bare graphene can be synthesized by any convenient and suitable technique, and no specific synthesis technique is required. In general, atmospheric chemical vapor deposition with methane gas on a catalyst material, e.g., a nickel layer, can be employed to form the graphene layer. Raman spectroscopy, transmission electron microscopy, and selected-area diffraction studies can be employed to verify that a region of synthesized graphene to be employed truly is single-layer in nature.

The transfer of the graphene layer to a device structure for arrangement as a graphene membrane can be conducted by any suitable technique, but it is preferred that any materials employed in the transfer do not corrupt the graphene surface. In one preferable technique, a selected handle material is coated over the synthesized graphene layer on the catalyst material and substrate. For many applications, it can be preferred to employ a handle material that is easily removed from the graphene surface once handling of the graphene layer is complete. Methyl methacrylite-methylacrylic acid co-polymer (MMA-MAA) can be a particularly well-suited handle material. With a layer of MMA-MAA in place on the graphene layer, the entire structure can be cut into pieces.

The resulting pieces can then be processed to remove the catalyst layer and substrate material underlying the graphene layer while adhered to the handle layer. For example, given a catalyst layer of Ni, an HCl solution can be employed to etch away the Ni layer and free the graphene/MMA-MAA composite, with distilled water employed to rinse. The graphene/MMA-MAA composite, floating on the water, can then be captured by, e.g., a silicon wafer coated with a $SiN_x$ layer. The central region of the silicon wafer can be etched by KOH or other suitable etchant to produce a free-standing $SiN_x$ membrane, e.g., of 50×50 $\mu m^2$ area. A focused ion beam (FIB) or other process can then be employed to drill a suitable hole through the $SiN_x$ membrane such that it forms a frame for the graphene layer membrane. For example, a square window of, e.g., 200 nm×200 nm can be formed in the nitride membrane to produce a frame for the graphene membrane.

With this device configuration complete, the graphene/MMA-MAA composite can be placed over the square window in the graphene membrane, employing, e.g., nitrogen wind (a gentle jet of nitrogen) to firmly press the graphene against the substrate. The MMA-MAA can then be removed, e.g., under a slow drip of acetone, followed by immersion in acetone, dichloroethane, and isopropanol.

It is preferable to remove any residues from the graphene film to reduce the tendency of species to adhere to the graphene once configured as a membrane. For example once the MMA-MAA is removed, the resulting structure including a graphene membrane outstretched across a nitride frame, as in FIG. 1, can be immersed in, e.g., a solution of KOH at room temperature briefly, e.g., for 1 min, and then vigorously rinsed with, e.g., water, then isopropanol, and finally ethanol. To avoid damage to the graphene membrane, the structure can be critical-point dried. Finally, the structure can be exposed to a selected environment, e.g., a rapid thermal annealing process at about 450° C. in a stream of gas containing 4% $H_2$ in He for, e.g., 20 minutes, to drive off any remaining hydrocarbons. To avoid recontamination, the structure preferably is then immediately loaded into, e.g., a TEM, for further processing.

A nanopore can then be formed in the graphene membrane. Focused electron beam or other process can be employed to form the nanopore. The nanopore diameter preferably is greater than the thickness of the graphene membrane, to obtain the benefits of the unexpected discovery of increased peripheral ionic current flow and increased sensitivity to change in molecular dimension as described above. For translocation of ssDNA, a nanopore diameter of between about 1 nm and about 20 nm can be preferred, with a diameter of between about 1 nm and about 2 nm most preferred. For translocation of dsDNA, a nanopore diameter of between about 2 nm and about 20 nm can be preferred, with a diameter of between about 2 nm and about 4 nm most preferred. After nanopore formation, it is preferred to keep the graphene structure under a clean environment, e.g., a vacuum of $\sim 10^{-5}$ Torr.

To complete the nanopore molecular sensing device of FIG. 1, the mounted graphene membrane can be inserted between two half-cells in, e.g., a microfluidic cassette of polyether-etherketone (PEEK) or other suitable material, sealed with, e.g., polydimethylsiloxane (PDMS) gaskets. It can be preferred that the gasket orifice be smaller than the dimensions of the graphene membrane to completely seal off the edges of the graphene membrane from the solutions.

Example I

This example describes an experimental demonstration of a single-layer, bare graphene membrane. A graphene layer was synthesized by CVD on a nickel surface. The nickel was provided as a film by E-beam evaporation on a silicon substrate coated with a layer of $SiO_2$. The nickel layer was thermally annealed to generate a Ni film microstructure with single-crystalline grains of sizes between about a 1 $\mu m$ and 20 $\mu m$. The surfaces of these grains had atomically flat terraces and steps, similar to the surface of single crystal substrates for epitaxial growth. With this topology, the growth of graphene on Ni grains resembles the growth of graphene on the surface of a single crystal substrate.

In the CVD synthesis, the Ni layer was exposed to $H_2$ and $CH_4$ gases at a temperature of about 1000° C. Raman spectroscopy, transmission electron microscopy and selected area diffraction studies showed the graphene film to be of excellent quality and mostly (87%) a mixture of one and two layer thick domains, with domain sizes of ~10 $\mu m$. Thicker regions of three or more graphene layers, easily distinguished by color contrast in an optical microscope, covered only a small fraction of the total surface. If thicker regions or domain boundaries were found, that area was discarded.

Graphene was transferred to a carrier Si/$SiN_x$ chip by first coating the graphene with MMA-MAA copolymer (MMA (8.5)MAA EL9, Microchem Corp.) and cut into 0.5 nm×0.5 mm pieces. These pieces were immersed for ~8 hr in 1N HCl solution to etch away the Ni film and free the graphene/polymer membrane, which was transferred to distilled water on which the graphene/polymer floated, graphene-side down. Carrier Si chips coated with ~250 nm thick $SiN_x$ were used to scoop up of the floating graphene/polymer film pieces, taking care that the graphene/polymer films were each stretched over the central region of a chip. The central region of the chip had been microfabricated using standard anisotropic etch techniques to leave a ~50×50 µm² area of the SiN$_x$ coating as a free-standing SiN$_x$ membrane into which a square window, ~200 nm×200 nm, had been drilled using a focused ion beam (FIB). A nitrogen gas wind was used to firmly press the graphene against the chip's surface. This led to expulsion of a small amount of liquid from under the graphene, which adhered strongly and irreversibly to the carrier chip's SiN$_x$ coating. The polymer on top of the graphene was removed under a slow drip of acetone, followed by subsequent immersions in acetone, dichloroethane, and finally isopropanol.

To remove any residues from the graphene film, each chip was subsequently immersed in 33 wt % solution of KOH at room temperature for 1 min and then vigorously rinsed with isopropanol and ethanol. To avoid damage to the suspended free-standing portion of the graphene film, each chip was critical-point dried. Finally, the chips were loaded into a rapid thermal annealer and heated to 450° C. in a stream of gas containing 4% H$_2$ in He for 20 minutes to drive off any remaining hydrocarbons. To avoid recontamination, the chips were immediately loaded into a transmission electron microscope for further processing.

Figure 4:
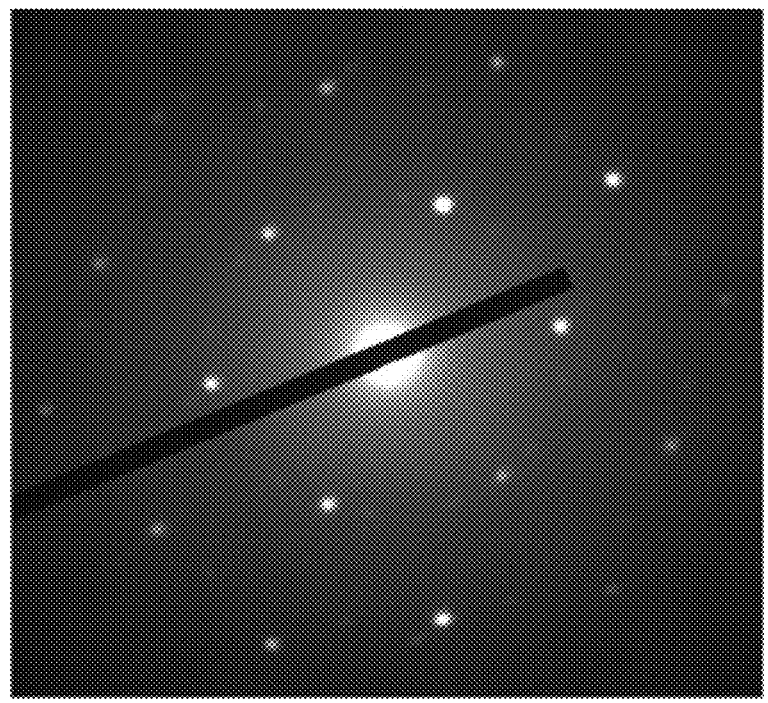
FIG. 4 is an X-ray diffraction image of an experimental graphene membrane, displaying the requisite hexagonal pattern that arises from the hexagonal packing of carbon atoms in a single graphene layer.
Figure 5:
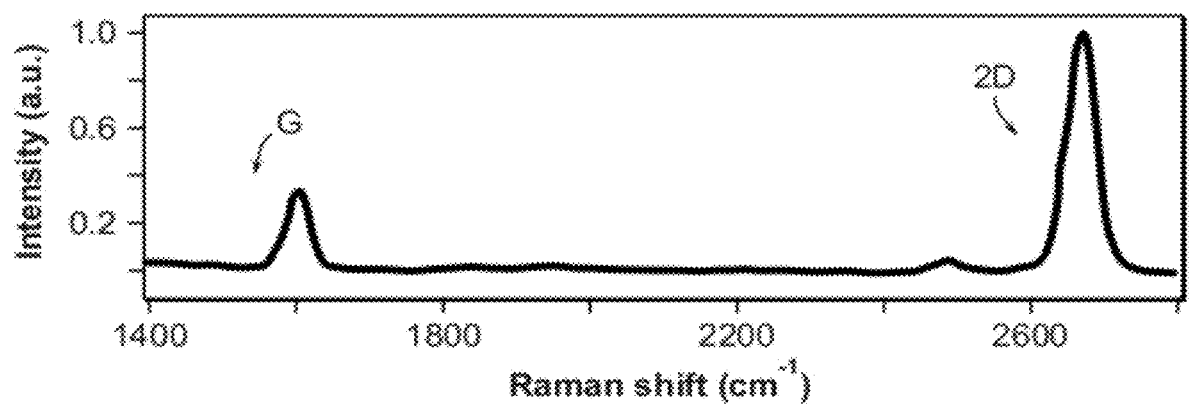
FIG. 5 is a plot of Raman shift measurements for an experimental graphene membrane indicating single-layer graphene for the membrane.

There is shown in FIG. 4 an X-ray diffraction image of one of the graphene membranes, displaying the requisite hexagonal pattern that arises from the hexagonal packing of carbon atoms in a single graphene layer. There is shown in FIG. 5 the Raman shift measurements for the graphene layer. The very small G peak and very sharp 2D peak, producing a G/2D ratio of less than 1, indicates a single-layer membrane.

Example II

This example describes an experimental determination of the conductance of the single-layer, bare graphene membrane of Example I.

A chip-mounted single-layer graphene membrane from Example I was inserted between the two half-cells of a custom-built microfluidic cassette made of polyether-etherketone (PEEK). The two sides of the chip were sealed with polydimethylsiloxane (PDMS) gaskets. The opening of the gasket that pressed against the graphene film on the Si/SiN$_x$ carrier chip had an inside diameter of ~100 µm. Consequently, the gasket orifice was smaller than the dimensions of the graphene membrane (0.5×0.5 mm²), and completely sealed off the graphene membrane edge from the electrolyte. On the opposite side of the chip, the electrolyte was in contact with the graphene membrane only through the 200 nm wide square window in SiN$_x$ membrane. Note that with this arrangement there was a large area difference between the two graphene membrane faces in contact with the electrolyte (a circular area of 100 µm diameter vs. a square 200 nm×200 nm area).

The two half-cells were first filled with ethanol to facilitate wetting of the chip surface. The cell was then flushed with deionized water, followed by 1M KCl salt solution with no buffer. To avoid any potential interaction between the graphene membrane and solutes which could affect experimental measurements, all electrolytes used in the experiment were kept as simple as possible and were unbuffered. All solution pHs ranged only 0.2 pH units, from 5.09 to 5.29, as measured both before and after use in the described experiments.

Ag/AgCl electrodes in each half-cell were used to apply an electric potential across the graphene membrane and to measure ionic currents. The current traces were acquired using an Axopatch 200B (Axon instruments) amplifier, which was connected to an external 8-pole Bessel low-pass filter (type 90IP-L8L, Frequency Devices, Inc.) operating at 50 kHz. The analog signal was digitized using a NI PCI-6259 DAQ card (National Instruments) operating at 250 kHz sampling rate and 16-bit resolution. All experiments were controlled through IGOR Pro software.

Figure 6:
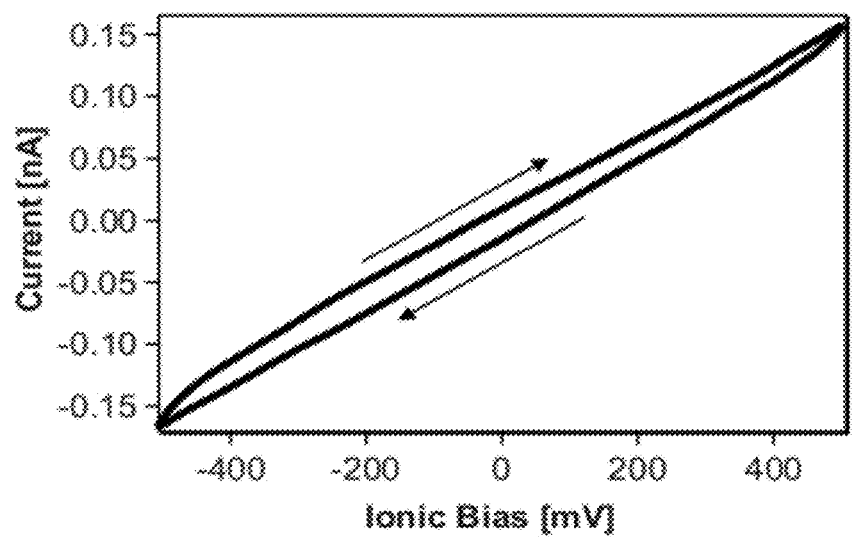
FIG. 6 is a plot of experimentally-measured data of ionic current as a function of the voltage bias applied between 3M KCl ionic solutions on the cis and trans sides of an experimental graphene membrane.

FIG. 6 is a plot of experimentally-measured data of ionic current as a function of the voltage bias applied between 3 M KCl ionic solutions on the cis and trans sides of the graphene membrane. Applying Ohm's Law to this data, it is found that the ionic current resistivity is well into the 3-4 G'Ω range perpendicular to the plane of the graphene membrane. This demonstrates one discovery of the invention that the ionic resistivity perpendicular to the plane of a graphene membrane is very large, and enables a configuration in which a significant electrical bias can be maintained across a bare, single-layer graphene membrane separating two voltage-biased ionic solution-filled reservoirs.

With a 100 mV bias applied between the two Ag/AgCl electrodes, ionic current measurements for a variety of chloride electrolytes on the cis and trans sides of the graphene membrane were conducted. Conductivities of the electrolytes were measured using an Accumet Research AR50 conductivity meter, which had been calibrated using conductivity standard solutions (Alfa Aesar, product #43405, 42695, 42679). All the fluidic experiments were performed under temperature controlled laboratory conditions, at 24° C. Table 1 shows that the graphene membrane's conductance is far below the nS level. The highest conductances were observed for solutions with the largest atomic size cations, Cs and Rb, correlated with a minimal hydration shell that mediates their interaction with the graphene. This conductance was attributed to ion transport through defect structures in the free-standing graphene membrane.

TABLE I

| Solution | Graphene Conductance (pS) | Sol. Conductivity ($10^{-3}$ Sm$^{-1}$) | Hydration energy (eV) |
|---|---|---|---|
| CsCl | 67 ± 2 | 1.42 | 3.1 |
| RbCl | 70 ± 3 | 1.42 | 3.4 |
| KCl | 64 ± 2 | 1.36 | 3.7 |
| NaCl | 42 ± 2 | 1.19 | 4.6 |
| LiCl | 27 ± 3 | 0.95 | 5.7 |

Contributions from electrochemical currents to and from the graphene membrane were ruled out by a further experiment Here, to investigate the contribution from electrochemical (Faradic) currents, a separate large-area graphene film (~2×4 mm²) was transferred to a glass slide and contacted at one end with silver paint attached to a metallic clip over which wax insulation was placed. The exposed end of the graphene film was immersed in 1M KCl electrolyte with a Ag/AgCl counter electrode, and the electrochemical I-V curves were measured in the same voltage range as used in the trans-electrode experiments. After normalizing for the surface area, it was concluded that any electrochemical currents in the trans-electrode devices were three orders of magnitude too small to account for the ~pA currents measured through the as-grown graphene membranes in Table 1. The observed conductances for different cations fall much faster than the solution conductivities on going from CsCl to LiCl, suggesting an influence of graphene-cation interactions. Nevertheless there cannot be completely ruled out ionic transport through graphene that is in contact with the chip surface.

Example III

This example describes an experimental determination of the conductance of the single-layer, bare graphene membrane of Example I including a nanopore.

A single nanometer-sized nanopore was drilled through several of the graphene membranes of Example I using a focused electron beam in a JEOL 2010 FEG transmission electron microscope operated at 200 kV acceleration voltage. The nanopore diameter was determined by EM visualization in a well-spread electron beam so as to keep the total electron exposure of the graphene membrane to a minimum. A nanopore diameter of 8 nm was determined as the average of 4 measurements along different nanopore axes, as determined from calibrated TE micrographs using DigitalMicrograph software (Gatan, Inc.). If the chip or TEM holder had any contaminating organic residue, amorphous carbon was seen to visibly deposit under the electron beam. Such devices were discarded. After drilling the nanopore, the graphene nanopore chips that were not immediately investigated were kept under a clean vacuum of ~$10^{-5}$ Torr.

Figure 7:
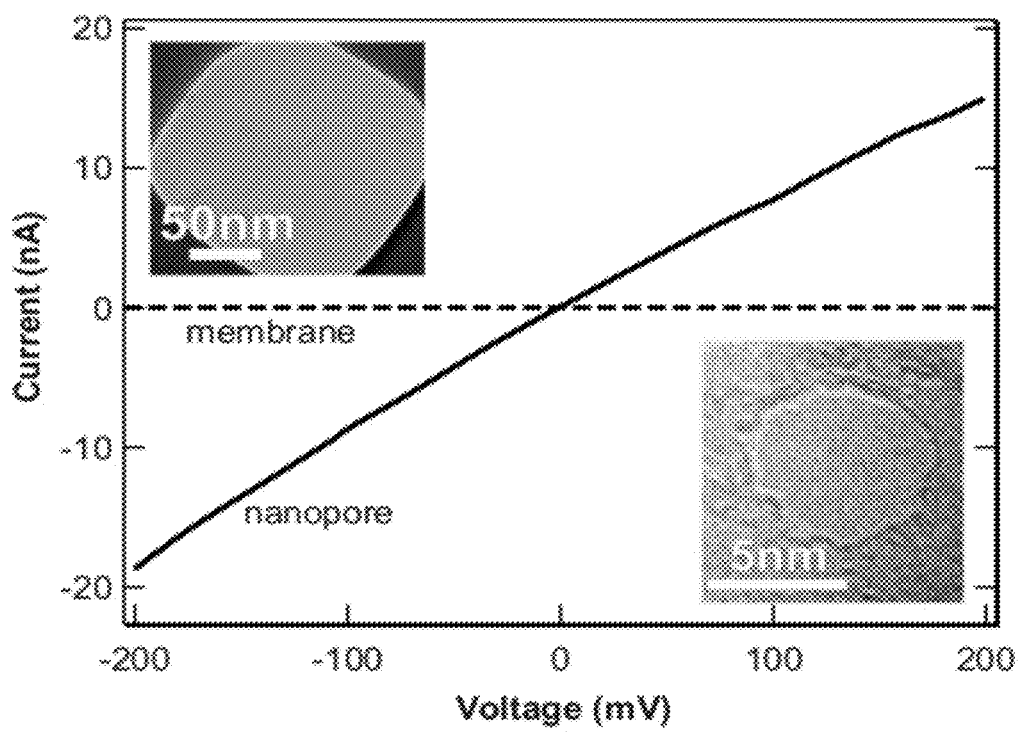
FIG. 7 shows the plot of FIG. 6 and a plot of ionic current as a function of voltage for an experimental graphene membrane including an 8 nm-wide nanopore.

FIG. 7 displays both a plot of ionic current as a function of applied voltage as given above in Example II for a continuous graphene membrane, as well as for a graphene membrane including an 8 nm-wide nanopore. These plots demonstrate that the ionic conductivity of the graphene membrane is increased by orders of magnitude by the nanopore.

Figure 8:
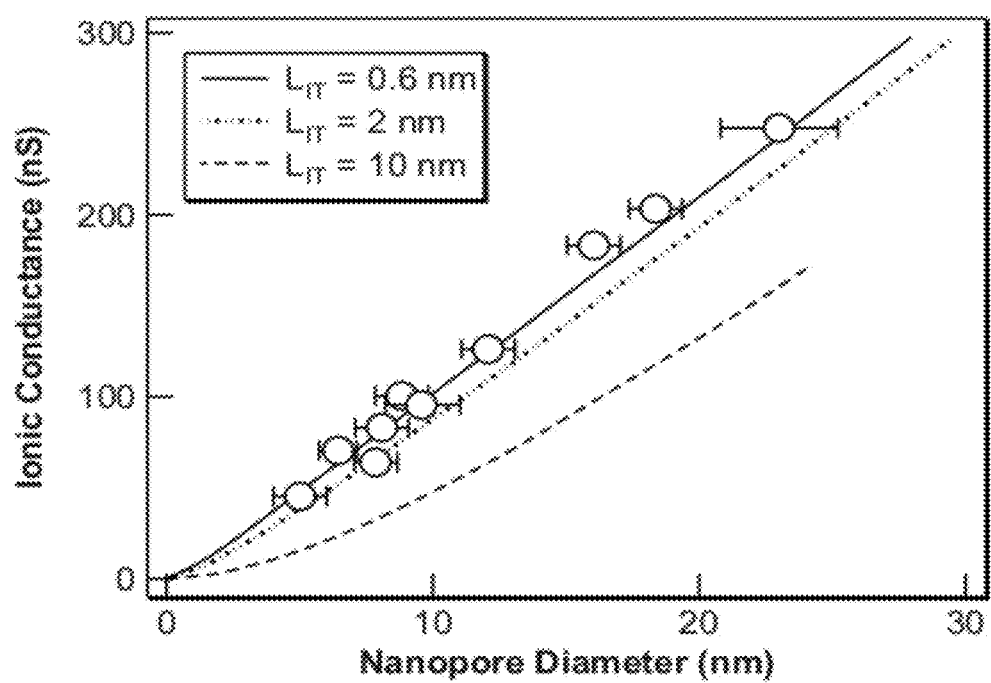
FIG. 8 is a plot of ionic conductance as a function of nanopore diameter for nanopores having a length of 0.6 nm, 2 nm, and 10 nm.

It is found that experiments with known graphene nanopore diameters and known ionic solution conductivities enable deduction of the bare, single-layer graphene membrane's effective insulating thickness. Ten separate graphene membranes from Example I were processed to include nanopore diameters ranging from 5 to 23 nm. Then the ionic conductance of each of the ten membranes was measured with a 1 M KCl solution provided for both cis and trans solution reservoirs, with a conductivity of 11 S m$^{-1}$. FIG. 8 is a plot of the measured ionic conductance as a function of nanopore diameter for the 10 membranes. The solid curve in the figure is the modeled conductance of a 0.6 nm-thick insulating membrane, which is the best fit to the experimentally measured conductances. The modeled conductance for a 2 nm-thick membrane is shown as a dotted line, and the modeled conductance for a 10 nm-thick membrane is shown as a dashed-dotted line, presented for comparison.

The ionic conductance, G, of a nanopore of diameter, d, in an infinitely thin insulating membrane is given by:

$$G_{thin} = \sigma \cdot d \qquad (1)$$

where $\sigma = F(\mu_K + \mu_{Cl})c$ is the conductivity of the ionic solution, F is the Faraday constant, c is ionic concentration, and $\mu_i(c)$ is the mobility of potassium (i=K) and chloride (i=Cl) ions used for a KCl ionic solution. The linear dependence of conductance on diameter follows from the current density being sharply peaked at the nanopore's perimeter for an infinitely thin membrane, as described above. For membranes thicker than the nanopore diameter the conductivity becomes proportional to the nanopore area. For finite but small thicknesses of membrane, computer calculations can predict the conductance.

As shown in the plot of FIG. 8, in agreement with Expression (1), the conductivities of the single-layer bare graphene nanopores with diameters ranging from 5 to 23 nanometers exhibited a near-linear dependence on nanopore diameter. The modeled curve was produced based on calculations of nanopore ionic conductivity in an idealized uncharged, insulating membrane, as a function of nanopore diameter and membrane thickness. Points on this curve were obtained by numerically solving the Laplace equation for the ionic current density, with appropriate solution conductivity and boundary conditions, and integrating over the nanopore area to get the conductivity. These numerical simulations were performed using the COMSOL Multiphysics finite element solver in appropriate 3-D geometry with cylindrical symmetry along the axis of the nanopore. The full set of Poisson-Nerst-Planck equations was solved in the steady-state regime. In the range of physical parameters of interest, high salt concentration and small applied voltage, the numerical simulation solution was found not to differ significantly from the solution of the Laplace equation with fixed conductance, which has significantly less computational penalty. The membrane thickness, L, used in this idealized model is herein referred to as graphene's Insulating Thickness, or $L_{IT}$. The best fit to the measured nanopore conductance data in FIG. 8 yields $L_{GIT}$=0.6 (+0.9–0.6) nm, with the uncertainty determined from a least square error analysis.

Example IV

This example describes experimental measurement of DNA translocation through a nanopore in a single-layer, bare graphene membrane of Example I.

The microfluidic cell of the examples above was flushed with 3M KCl salt solution at pH 10.5, containing 1 mM EDTA. As explained above, high salt concentration and high pH were found to minimize DNA-graphene interaction and thus these solution conditions can be preferred. 10 kbp restriction fragments of double-stranded lambda DNA molecules were introduced to the cis chamber of the system. The negatively charged DNA molecules were electrophoretically drawn to and driven through the nanopore by the applied electrophoretic force of 160 mV. Each insulating molecule passing through the nanopore transiently reduced, or blocked, the ionic conductivity of the nanopore in a manner that reflects both polymer size and conformation. As the DNA fragments traversed the nanopore due to the applied electrophoretic force, the translocation events were analyzed with MATLAB using a fitting function that consisted of multiple square pulses convoluted with an appropriate Bessel filter function to mimic the recording conditions.

Figure 9:
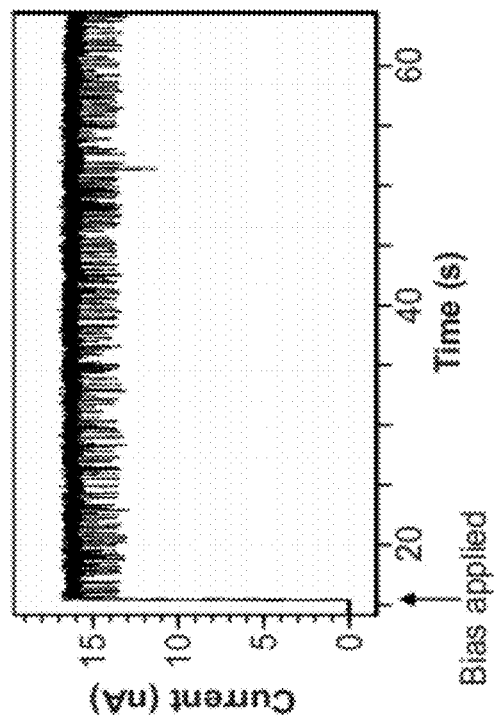
FIG. 9 is a plot of measured ionic current as a function of time for a 2.5 nm nanopore in an experimental graphene membrane as DNA fragments translocate through the nanopore.

FIG. 9 is a plot of measured ionic current through the nanopore as a function of time for one minute from the time a voltage bias was applied between the cis and trans reservoirs. Each drop in measured current in the plot corresponds to a DNA translocation through the nanopore, and enables characterization of two parameters, namely, the average current drop, or blockade, and the duration of the blockade, which is the time it takes for the molecule to completely translocate through the nanopore. Note the high number of translocation events for the bare graphene membrane nanopore in the one minute time period, indicating successful inhibition of DNA adherence to the bare graphene membrane surface with the high pH salt solution and the careful cleaning and handling of the graphene membrane during preparation for the DNA translocation experiments.

Figure 10C:
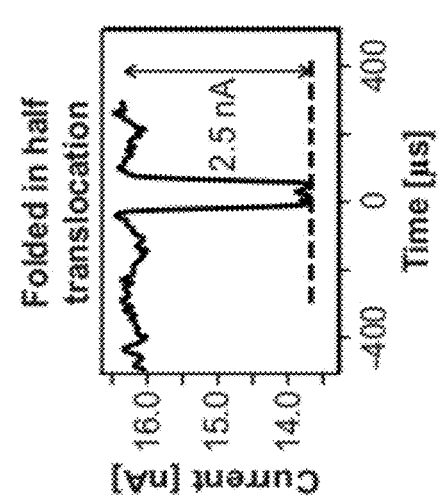
FIGS. 10A-10C are plots of measured ionic current as a function of time taken from the plot of FIG. 9, showing in detail the current profile for DNA nanopore translocation in single-file fashion, in partially-folded fashion, and folded in half.
Figure 10B:
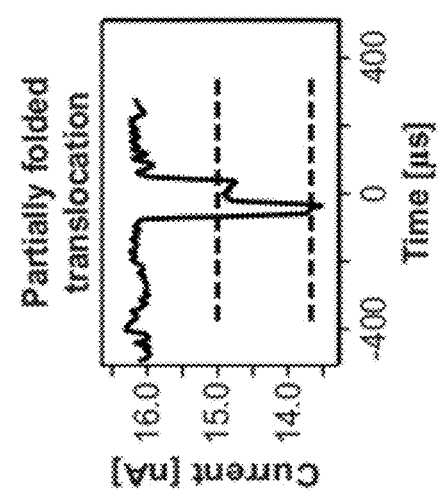
Figure 10A:
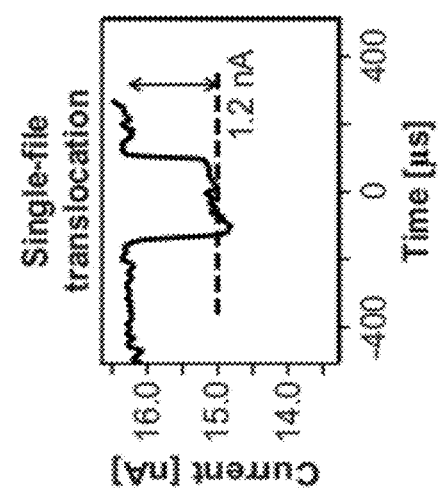

FIGS. 10A, 10B, and 10C are plots of measured ionic current through the nanopore for single translocation events. In FIG. 10A there is demonstrated the ionic current flow blockage during a translocation of DNA in single-file fashion. In FIG. 10B there is demonstrated the ionic current flow blockage during translocation of DNA that has been partially folded. Finally, in FIG. 10C there is demonstrated the ionic current flow blockage during translocation of DNA that has been folded in half. These three experimental translocation events typify the possible ionic current flow measurements that can occur during translocation of DNA fragments, and demonstrates that DNA folding and conformation can occur with the graphene nanopore as with thicker conventional solid state nanopores.

Figure 11:
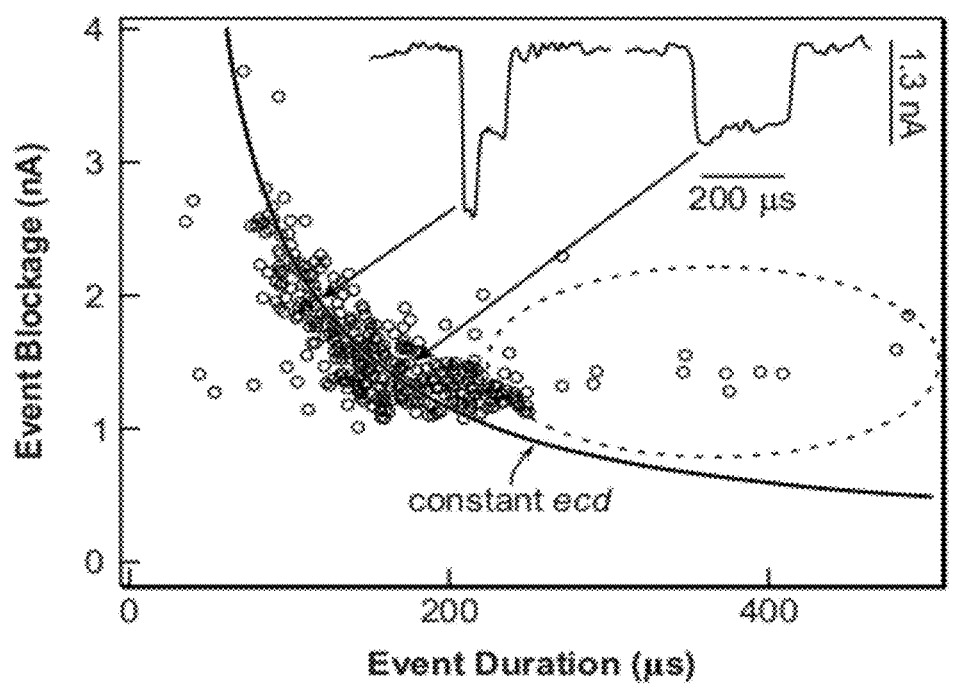
FIG. 11 is a plot of ionic current blockage as a function of DNA translocation of a nanopore in a graphene membrane for 400 translocation events.

A 5 nm-wide nanopore was formed in a separate graphene membrane from Example I and double-stranded DNA translocation experiments were conducted for the 3 M KCl solution of pH 10.4. Each single molecule translocation event can be characterized by two parameters: the average current drop, or blockade, and the duration of the blockade, which is the time it takes for the molecule to completely translocate through the pore. FIG. 11 is a scatter plot showing the value of current drop and blockade duration for each of 400 double stranded DNA single molecule translocations through the graphene nanopore. The characteristic shape of this data is similar to that obtained in silicon nitride nanopore experiments where almost all the events, folded and unfolded, fall near a line of constant electronic charge deficit (ecd), i.e., regardless of how the otherwise identical molecules are folded, each blocks the same amount of ionic charge movement through the nanopore during the total time it takes each molecule to move through the nanopore. Here as in the previous experiment it is demonstrated that the double stranded DNA passed through the nanopore uninhibited by sticking to the graphene surface. The few events that are encircled in the plot do not satisfy this condition and their long translocation times indicate graphene-DNA interactions, which slow their translocation through the nanopore.

In the plot of FIG. 11 the insets show two single-molecule translocation events. In the right-hand event a molecule passed through the nanopore in an unfolded linear fashion, as in the example of FIG. 10A. In the left-hand event the molecule was folded over on itself when it entered the nanopore as in the example of FIG. 10B, increasing the current blockade for a short time.

Measurements of nanopore conductance during DNA translocation events can be employed as an alternative method for evaluating the effective insulting thickness of the graphene membrane, $L_{IT}$. The experimentally-determined open-nanopore and DNA-blocked nanopore conductance was compared with that determined by numerical solutions, where the membrane thickness and the nanopore diameter are the fitting parameters. Here a DNA molecule was modeled as a long, stiff, insulating rod of diameter 2 nm which threads through the center of a nanopore. For lateral resolution calculations, there was added a step of 2.2 nm in diameter to the DNA model, and the change in the ionic current was calculated as the discontinuity translocates through the center of the nanopore. The total ionic current was calculated by integrating current density across the diameter of the nanopore.

Using the observed mean current blockade, $\Delta I=1.24\pm0.08$ nA during translocation of unfolded double-stranded DNA of diameter 2.0 nm, and the observed conductance of the nanopore $G=105\pm1$ nS absent DNA, the graphene membrane insulating thickness was determined as $L_{IT}=0.6\pm0.5$ nm, in excellent agreement with the value deduced above from open nanopore measurements alone, as discussed above. The nanopore diameter $d_{GIT}=4.6\pm0.4$ nm deduced from these calculations also agrees with the geometric diameter of $5\pm0.5$ nm obtained from a TEM of the nanopore.

The best fit value $L_{IT}=0.6$ nm from both experiments agrees with molecular dynamics simulations showing the graphene-water distance to be 0.31-0.34 nm on each side of the membrane. $L_{IT}$ might also be influenced by the typical presence of immobilized water molecules and adsorbed ions in the Stern layer. On the other hand, theoretical studies argue against any immobilized water layer on graphene, and experimental measurements support an anomalously high slip between water and an internal curved carbon nanotube surface. Although very little is actually known about the surface chemistry of specifically adsorbed ions on bare single graphene layers, measurements of the ionic current through the inner volume of carbon nanotubes with diameters less than 1 nm may indicate that ions are not immobilized on these graphitic surfaces at all. The sub-nanometer values for $L_{IT}$ determined here support this view.

The extremely small value for $L_{IT}$ obtained here suggests that nanopores in single-layer, bare graphene membranes are uniquely optimal for discerning spatial and/or chemical molecular structure along the length of a molecule as it passes through the nanopore. Numerical modeling of the molecular detection resolution obtainable by such a nanopore can be accomplished based on the determination of graphene membrane insulating thickness, $L_{IT}$.

Figure 12:
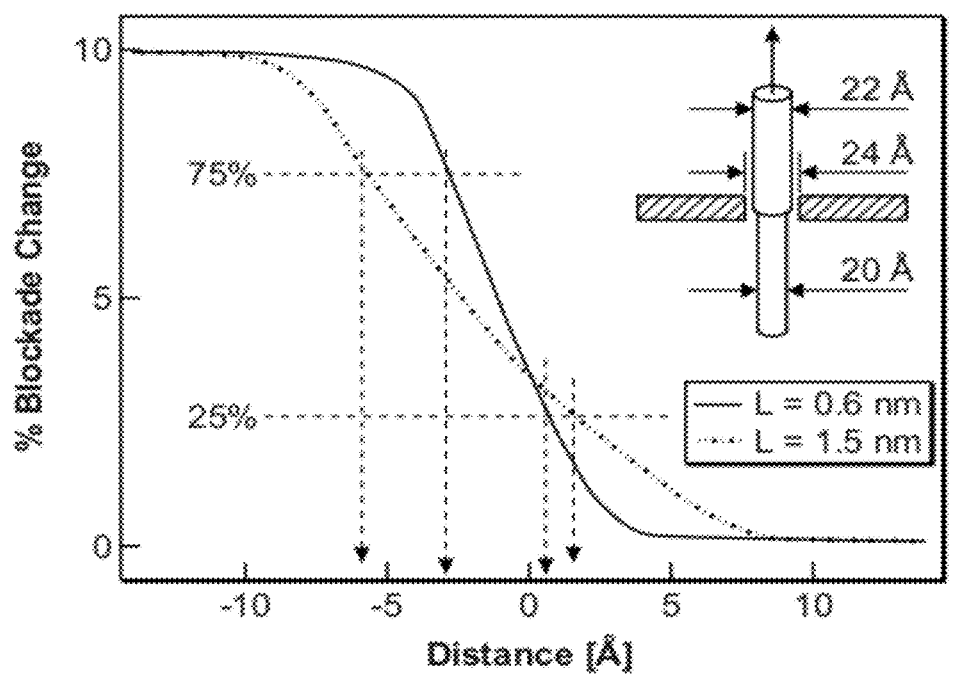
FIG. 12 is a plot of the percentage change in ionic current blockade as a function of distance through a nanopore, for a 0.6 nm-long nanopore and for a 1.5 nm-long nanopore.

In an example of such a model, there is specified a long, insulating, 2.2 nm-diameter cylinder that symmetrically translocates through the center of a 2.4 nm-diameter nanopore. At one position along its length, the cylinder diameter changes discontinuously from 2.2 nm to 2.0 nm. Solving for the conductance for this geometry as the discontinuity passes through the pore, there is obtained the data shown in the plot of FIG. 12. The decreasing ionic current flow blockade, corresponding to increasing nanopore conductance, is clearly seen as the large diameter portion of the molecular cylinder exits the nanopore. The results of calculations for two $L_{IT}$ values are shown. For the conservative $L_{IT}=1.5$ nm, the spatial resolution, defined as the distance over which the conductivity changes from 75% of its greatest value to 25% of that value, is given by $\delta z_{GIT}=7.5$ Å, whereas the best-fit value $L_{GIT}=0.6$ nm leads to $\delta z_{GIT}=3.5$ Å.

There can be concluded both from the experiments detailed above as well as from the modeling described above that a nanopore in a bare single-layer graphene membrane is inherently capable of probing molecules with sub-nanometer resolution. Functionalizing the graphene nanopore boundary or observing its local in-plane ionic conductivity during translocations can provide additional or alternative means of further increasing the resolution of this system.

From the description above, it has been demonstrated that an atomically thin sheet of bare, single-layer graphene can be fabricated into a self-supporting membrane including a nanopore, of a diameter larger than the membrane thickness, for sensing molecular translocation events through the nanopore. As a bare, single layer, the thickness of the graphene membrane is minimized and is safely in the short-length nanopore regime in which peripheral ionic current flow is maximized and in which the nanopore conductivity as a function of nanopore length is maximized. The very short nanopore length provided by the graphene membrane also makes it possible for a graphene nanopore to sense closely-spaced monomers in a polymer and thus to sequentially resolve the different ionic blockages caused by each monomer in, for example, a strand of a DNA polymer.

Based on these considerations, it is recognized that if technological advances enable such, a solid state membrane of an alternative material can be substituted for the single-layer, bare graphene membrane layer. Specifically, a solid state membrane having a thickness that is less than about 1 nm and that can mechanically support a nanopore extending through the membrane thickness with a diameter that is greater than the membrane thickness can be employed to obtain the molecular sensing capability described above, and in particular, the DNA sensing capability. It is to be understood that the requirements for resistivity perpendicular to the plane of the membrane, the mechanical integrity, and other characteristics described above can be required to enable the arrangement of the membrane material between cis and trans reservoirs for molecular translocation though the membrane nanopore. Ionic current blockage measurement or other electrical measurement can be employed as-suitable for a given application and no particular measurement technique is required.

For many molecular sensing applications, the solid state membrane can be provided as a nanometric material that is less than about 5 nanometers in thickness. Such nanometric materials include, e.g., atomically-thin materials, which in general can be described as materials having a thickness of an atomic monolayer or a few atomic layers, such as a bilayer or trilayer of atoms. A mono-atomically-thick material is herein defined as a material which is one atom in thickness, but need not be atoms of just one element. Atoms of a plurality of different elements can be included in an atomic layer. The mono-atomically-thick layer can be decorated at the layer top and/or bottom with heterogeneous atoms and other species that do not lie in the plane of the atoms.

Such atomically-thin materials include, e.g., two-dimensional free-standing atomic crystals, and other structures having a characteristic unit, like a lattice constant, that is repeating in two dimensions but not the third. Atomically-thin materials also include non-crystalline materials, such as glassy materials for which a mono-atomic layer and few-atomic-layers can be formed. Other example nanometric materials include materials that are a single molecule in thickness, or that are two or three molecules in thickness.

Beyond the example nanometric material graphene that has been described above, other nanometric materials that can be employed include fluorographene, graphane, graphene oxide, hexagonal boron nitride (hexagonal-BN), mono-atomic glasses, and other such materials. Other suitable nanometric materials include, e.g., $MoS_2$, $WS_2$, $MoSe_2$, $MoTe_2$, $TaSe_2$, $NbSe_2$, $NiTe_2$, $Bi_2Sr_2CaCu_2O_x$, and $Bi_2Te_3$. These are representative examples of suitable nanometric solid state materials but are not limiting; any suitable nanometric material in which or more nanopores can be formed for molecular analysis in the configuration of FIG. 1 can be employed.

Extending this understanding further, it is recognized that alternative configurations to a nanopore can be employed. For example, a membrane or other structure in which there can be produced an aperture having a very sharp or pointed edge location at which the aperture diameter is reduced to the nanometer scale, and which is larger than the thickness of the location of the diameter reduction, can also be employed. Thus, any solid state structural configuration in which an aperture can be configured meeting these requirements can be employed to achieve the advantages for molecular sensing described above.

It is recognized, of course, that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A graphene nanopore sensor comprising:
   a substantially bare, self-supported, single-layer graphene membrane having an ionic conductance between about 27 pS to 70 pS, the graphene membrane including a nanopore with a diameter of between about 1 nm and about 2 nm extending through a thickness of the graphene membrane from a first graphene membrane surface to a second graphene membrane surface opposite the first graphene membrane surface;
   a first reservoir including at least one species selected from the group consisting of DNA and RNA in an ionic solution having a pH between about 8.5 and 11 and a salt concentration greater than about 2 M, the first reservoir disposed in fluidic connection with the membrane whereby the first graphene membrane surface and the nanopore are exposed to the ionic solution and species in the ionic solution in the first reservoir;
   a second reservoir including an ionic solution having a pH between about 8.5 and 11 and a salt concentration greater than about 2 M, the second reservoir disposed in fluidic connection with the membrane whereby the second graphene membrane surface and the nanopore are exposed to the ionic solution in the second reservoir, and the second reservoir arranged to collect the species and ionic solution after translocation of the species and ionic solution through the nanopore from the first graphene membrane surface to the second graphene membrane surface; and
   an electrical circuit connected with the nanopore through said thickness of the graphene membrane from the first reservoir to the second reservoir to measure flow of ionic current through the nanopore in the graphene membrane.

2. The graphene nanopore sensor of claim 1 wherein the electrical circuit is connected between the ionic solution in the first reservoir and the ionic solution in the second reservoir to measure flow of ionic current through the nanopore in the graphene membrane.

3. The graphene nanopore sensor of claim 1 wherein the electrical circuit includes an electrical current monitor connected for measuring time-dependent ionic current flow through the nanopore.

4. The graphene nanopore sensor of claim 3 wherein the electrical current monitor is connected for measuring time-dependent ionic current flow blockages indicative of species translocation through the nanopore.

5. The graphene nanopore sensor of claim 1 further comprising an electrode disposed in the ionic solution in each of the first and second reservoirs for applying a voltage between the first and second reservoirs to electrophoretically cause species translocation through the nanopore.

6. The graphene nanopore sensor of claim 1 wherein the ionic solution is KCl.

7. The graphene nanopore sensor of claim 1 wherein the graphene membrane is characterized by a thickness that is less than about 1 nm.

8. The graphene nanopore sensor of claim 1 wherein the graphene membrane is characterized by a thickness that is less than about 0.7 nm.

9. The graphene nanopore sensor of claim 1 wherein the nanopore is characterized by a diameter that is no more than about 5% larger than a diameter of the species in the ionic solution.

10. The graphene nanopore sensor of claim 1 wherein the graphene membrane is mechanically supported at edges of the membrane by a membrane frame structure.

11. A graphene nanopore sensor comprising:
a substantially bare, self-supported, single-layer graphene membrane having an ionic conductance between about 27 pS to 70 pS, the graphene membrane including a nanopore extending through a thickness of the graphene membrane from a first graphene membrane surface to a second graphene membrane surface opposite the first graphene surface and having a diameter that is no greater than about 4 nm and greater than the graphene thickness;
a first reservoir including polymer molecules in an ionic solution having a pH between about 8.5 and 11 and having a salt concentration greater than about 2 M, the polymer molecules having a polymer molecule diameter, with the first graphene membrane surface and the nanopore exposed to the ionic solution and polymer molecules in the ionic solution of the first reservoir and the nanopore having a nanopore diameter that is no more than about 5% larger than the diameter of the polymer molecules in the ionic solution;
a second reservoir, the second reservoir including an ionic solution having a pH between about 8.5 and 11 and having a salt concentration greater than about 2 M, with the second graphene membrane surface and the nanopore exposed to the ionic solution in the second reservoir, the second reservoir arranged to collect the polymer molecules and the ionic solution after translocation of the polymer molecules and the ionic solution through the nanopore from the first graphene membrane surface to the second graphene membrane surface; and
an electrical circuit connected with the nanopore through said thickness of the graphene membrane from the first reservoir of ionic solution to the second reservoir of ionic solution to measure flow of ionic current through the nanopore in the graphene membrane.

12. The graphene nanopore sensor of claim 11 wherein the species in the ionic solution to translocate through the nanopore comprises biomolecules.

13. The graphene nanopore sensor of claim 11 wherein the species in the ionic solution to translocate through the nanopore comprises DNA molecules.

14. The graphene nanopore sensor of claim 11 wherein the species in the ionic solution to translocate through the nanopore comprises RNA molecules.

15. The graphene nanopore sensor of claim 11 wherein the species in the ionic solution to translocate through the nanopore comprises oligonucleotides.

16. The graphene nanopore sensor of claim 11 wherein the species in the ionic solution to translocate through the nanopore comprises a protein.

17. The graphene nanopore sensor of claim 11 wherein the species in the ionic solution to translocate though the nanopore comprises nucleotides.

18. The graphene nanopore sensor of claim 11 wherein the electrical current monitor is connected for measuring time-dependent ionic current flow blockages indicative of polymer molecule translocation through the nanopore.

19. The graphene nanopore sensor of claim 11 further comprising an electrode disposed in the ionic solution in each of the first and second reservoirs for applying a voltage between the first and second reservoirs to electrophoretically cause species translocation through the nanopore.

20. A nanopore sensor comprising:
a substantially bare, self-supported, single-layer graphene membrane having an ionic conductance between about 27 pS to 70 pS, the graphene membrane having a thickness, between a first membrane surface and a second membrane surface opposite the first membrane surface, that is less than about 1 nm;
a nanopore extending through the membrane thickness between the first and second membrane surfaces and having a diameter that is greater than the membrane thickness;
a first reservoir including a species in an ionic solution having a pH between about 8.5 and 11 and a salt concentration of at least about 2 M, the species having a species diameter, with the first membrane surface and the nanopore exposed to the ionic solution and species in the ionic solution in the first reservoir and the nanopore having a nanopore diameter that is no more than about 5% larger than the diameter of the species in the ionic solution;
a second reservoir including an ionic solution having a pH between about 8.5 and 11 and a salt concentration of at least about 2 M, with the second membrane surface and the nanopore exposed to the ionic solution in the second reservoir, the second reservoir arranged to collect the species and ionic solution after translocation of the species and ionic solution through the nanopore from the first membrane surface to the second membrane surface; and
an electrical circuit connected with the nanopore through said thickness of the membrane from the first reservoir to the second reservoir to monitor translocation of the species in the ionic solution through the nanopore in the solid state membrane.

21. The nanopore sensor of claim 20 wherein the nanopore is characterized by a diameter that is between about 1 nm and about 10 nm.

22. The nanopore sensor of claim 20 wherein the nanopore is characterized by a diameter that is between about 1 nm and about 5 nm.

23. The nanopore sensor of claim 20 wherein the nanopore is characterized by a diameter that is no greater than about 4 nm.

24. The nanopore sensor of claim 20 wherein the nanopore is characterized by a diameter that is less than about 2.5 nm.

* * * * *